US005832447A

United States Patent [19]
Rieker et al.

[11] Patent Number: 5,832,447
[45] Date of Patent: Nov. 3, 1998

[54] AUTOMATED SYSTEM AND METHOD FOR PROVIDING REAL-TIME VERIFICATION OF HEALTH INSURANCE ELIGIBILITY

[75] Inventors: Edward C. Rieker, Decatur; Daniel K. Mansfield, Duluth, both of Ga.

[73] Assignee: Envoy Corporation, Nashville, Tenn.

[21] Appl. No.: 248,459

[22] Filed: May 24, 1994

[51] Int. Cl.[6] .................................................. G06F 13/00
[52] U.S. Cl. ..................................... 705/2; 705/4
[58] Field of Search ........................... 364/401, 413.01, 364/413.02; 235/378, 380, 375, 494; 395/200.01, 670, 200.3

[56] References Cited

U.S. PATENT DOCUMENTS

| | | |
|---|---|---|
| 4,491,725 | 1/1985 | Pritchard . |
| 4,645,916 | 2/1987 | Raisleger .............................. 235/494 |
| 4,667,292 | 5/1987 | Mohlenbrock et al. . |
| 4,837,693 | 6/1989 | Schotz . |
| 4,858,121 | 8/1989 | Barber et al. . |
| 4,916,611 | 4/1990 | Doyle, Jr. et al. . |
| 4,975,840 | 12/1990 | DeTore et al. . |
| 4,987,538 | 1/1991 | Johnson et al. . |
| 5,070,452 | 12/1991 | Doyle, Jr. et al. . |
| 5,140,518 | 8/1992 | Ema . |
| 5,191,522 | 3/1993 | Bosco et al. . |
| 5,225,976 | 7/1993 | Tawil . |
| 5,230,048 | 7/1993 | Moy ........................................ 395/600 |
| 5,235,507 | 8/1993 | Sackler et al. . |
| 5,235,702 | 8/1993 | Miller . |
| 5,241,625 | 8/1993 | Epard et al. ............................ 395/163 |

OTHER PUBLICATIONS

Shoor, "Moving Health Care Data Electronically", 10 *Business & Health* v. 10, n. 12, pp. 38–44 (Oct. 1992).

*Primary Examiner*—Gail O. Hayes
*Assistant Examiner*—Phillip Grouttt
*Attorney, Agent, or Firm*—Nixon & Vanderhye P.C.

[57] ABSTRACT

Data from a health care provider computer system is used to automatically request real-time electronic insurance eligibility verification information from health care insurance payors. A patient health insurance verification computer system is operatively connected to a patient registration computer system. The verification computer system obtains a data output stream such as a print image from the registration computer system. This data output stream is captured and broken down into separate data fields. The insurance carrier is determined, and the verification computer system determines which electronic data source to request patient eligibility data from. The verification computer system reformats the captured data to fit the data format required by the data source, establishes a communications link to the data source, and sends the reformatted data to the data source. The data source sends responsive patient specific eligibility data which the verification computer system uses to automatically verify insurance coverage. Health insurance verification becomes much more reliable since no human intervention is required to carry on the automatic verification process. Additionally, automatic verification can be performed conveniently without double data entry even in environments with preexisting admissions systems that cannot be easily modified.

18 Claims, 19 Drawing Sheets

HARDWARE CONNECTIONS

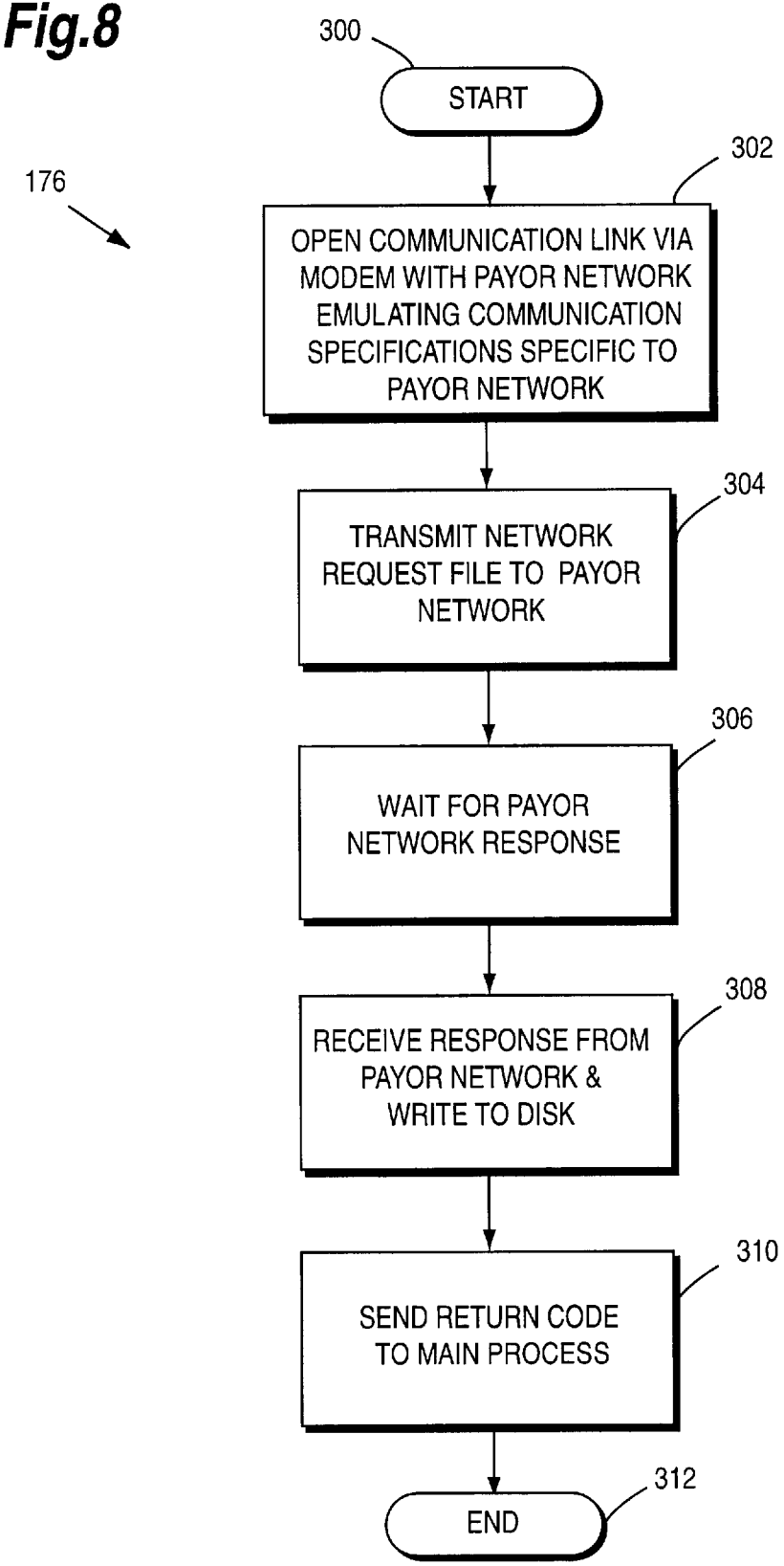

Fig. 9B

| TRANSACTION REQUEST TABLE | 400 |
|---|---|
| PATIENT REQUEST ID | 402 |
| PATIENT MIDDLE INITIAL | 404 |
| PATIENT LAST NAME | 406 |
| PATIENT SUFFIX NAME | 408 |
| RELATION CODE | 410 |
| BILLING NUMBER | 412 |
| PATIENT NUMBER | 414 |
| PATIENT DATE OF BIRTH | 416 |
| PATIENT SEX | 418 |
| BENEFIT CODE | 420 |
| FROM DATE | 422 |
| TO DATE | 424 |
| INSURED FIRST NAME | 426 |
| INSURED MIDDLE INITIAL | 428 |
| INSURED LAST NAME | 430 |
| INSURED SUFFIX NAME | 432 |
| INSURED SSN | 434 |
| INSURED MEMBER ID | 436 |
| INSURED ID | 438 |
| INSURED EMPLOYER NAME | 440 |
| INSURED EMPLOYER GROUP | 442 |
| PROVIDER NETWORK NUMBER | 444 |
| PAYOR ID | 446 |
| PAYOR NAME ON FORM | 448 |
| TIME ADDED | 450 |
| TIME REQUEST INITIATED | 452 |
| TIME REQUEST COMPLETED | 454 |
| RESPONSE COUNT | 456 |
| LOOKUP CODE | 458 |
| NETWORK ID | 460 |
| MAIL BOX FLAG | 462 |
| REQUEST FILE NAME | 464 |
| TRY COUNT | 466 |

Fig. 10A

| 4 PATIENT'S LEGAL NAME (L, F MI) | | 5 SEX | 6 RACE | 7 BIRTH DATE | 1 MEDICAL RECORD NO | 2 BILLING NO | | 3 A R NO | IS530.91 (REV 4-60) |
|---|---|---|---|---|---|---|---|---|---|
| 14 | | | | | 8 AGE | 9 HEIGHT | 10 WEIGHT | 11 SS | 12 MS | 13 RELIGION CHURCH | |
| | 15 PATIENT'S LEGAL ADDRESS | | | | | CITY/STATE | | | 16 TELE |
| 17 ES | 18 PATIENT'S EMPLOYER | | | | | | | | |
| | 19 EMPLOYER ADDRESS | | | | | CITY/STATE | | | 20 TELE |
| 21 SOCIAL SECURITY NO | 22 EMPLOYEE ID | 23 LOE | 24 OCCUPATION | | 25 | 26 LOR | 27 COUNTY CODE | 28 COUNTY | 32 TELE |
| 29 PR | 30 RESPONSIBLE PARTY | | 31 RESPONSIBLE PARTY'S ADDRESS | | | CITY/STATE | | | |
| 33 ES | 34 RESPONSIBLE PARTY'S EMPLOYER | | 35 EMPLOYER ADDRESS | | | CITY/STATE | | | 36 TELE |
| 37 SOCIAL SECUTIY NO | 38 EMPLOYEE ID | 39 LOE | 40 OCCUPATION | | 41 | 42 LOR | 43 COUNTY CODE | 44 COUNTY | |
| 45 PR | 46 OTHER PARTY | | 47 OTHER PARTY'S ADDRESS | | | CITY/STATE | | | 48 TELE |
| 49 ES | 49 OTHER PARTY'S EMPLOYER | | 51 EMPLOYER ADDRESS | | | CITY/STATE | | | 52 TELE |
| 53 SOCIAL SECURITY NO | 54 EMPLOYEE ID | 55 LOE | 56 OCCUPATION | | 57 | 58 LOR | 59 COUNTY CODE | 60 COUNTY | |
| | | | 64 CLAIM PROCESSING ADDRESS | | | | CITY/STATE | | |
| 61 INS CODE | 62 SP | 63 PAYER | | 66 REL INFO | 67 ASG BEN | 68 SP PROG | 69 CONDITIONS | 70 CD | 71 FROM | OCCURRENCE | 72 THROUGH |
| 65 INSURED | | | | | | | | | |
| 73 CERTIFICATE/SSN/HIC ID NO | 74 GROUP NAME | | | | 75 INSURANCE GROUP NO | | 76 TREATMENT AUTH | | |
| 77 COVERAGE | | | | | | | | | |

PRIMARY →

AUTOMATED SYSTEM AND METHOD FOR PROVIDING REAL-TIME VERIFICATION OF HEALTH INSURANCE ELIGIBILITY

FIELD OF THE INVENTION

The present invention relates to automatic insurance eligibility determination, and more specifically, to method and apparatus for automatically determining in real-time whether a patient at a health care facility has health insurance coverage.

BACKGROUND AND SUMMARY OF THE INVENTION

Currently, hospitals and health care providers have a real problem determining whether patients are eligible for health insurance coverage. When a patient seeks health care at a hospital, the admitting staff usually asks the patient whether the patient has health insurance. Often, the admitting staff will ask the patient for evidence of health insurance eligibility (e.g., a medical insurance card or the like). Information corresponding to the health insurance coverage the patient says he has is inputted into the hospital's computerized patient admissions system. However, there is no easy, reliable way to verify this coverage at the time the patient is admitted. Health insurance coverage, such as Medicaid and Medicare, is often determined on a periodic basis (e.g., weekly or monthly) so that the insurance rolls are constantly changing. For this reason, it is important for hospitals and other health care providers to obtain timely, accurate and complete health insurance eligibility information for each incoming patient.

The admissions clerk could pick up a telephone and dial the telephone number of an information service or the patient's asserted health care provider to obtain a verbal response verifying insurance coverage. Alternatively, many hospitals and other health care providers have "POS" ("point of sale") terminals and/or personal computers that can link electronically over telephone lines with "information providers" sometimes called "clearinghouses" that verify health insurance coverage eligibility. However, these techniques require the admitting clerk to decide to check health insurance eligibility, and then take additional steps necessary to verify. Thus, these techniques suffer from the drawback that verifying insurance eligibility is not automatic. If the admissions clerk is busy, he or she may not have sufficient time to verify the eligibility of some or all incoming patients. Thus, many problems arise later on when the hospital's billing department tries to collect from the insurance company, and in the worst case, can cause the hospital to lose the ability to recover costs and fees for health care.

FIG. 1 is a schematic illustration of a typical prior art insurance eligibility verification "network." The right-hand side of the figure shows a large number of different health insurance payors. Some patients may be self-insured through their businesses, for example, while other patients have insurance through conventional health insurance companies. Other patients may be insured by the Federal Government or a state government (i.e., Medicaid or Medicare). Each one of these various insurers may periodically make eligibility information available to "data gateway" value added networks. These data gateways are sometimes called "clearing houses" because they receive insurance eligibility information from one or a number of health insurers, and make the eligibility information available to doctors' offices, hospitals, clinics, and other health care providers via telecommunications links. While clearinghouses provide added dissemination of insurance eligibility information, the proliferation of health insurers has also caused the clearing houses to proliferate. Thus, it is typically necessary to obtain information about certain particular health insurers from data gateway 1, to obtain eligibility for certain other health insurers from a different data gateway 2, etc. To make matters even more complicated, the different data gateways typically each have their own proprietary digital communications protocol, and may provide their own POS terminals or personal computer software for accessing the gateways. As a result, many hospital admissions offices have several POS terminals, one for each of the various data gateways from which the hospital routinely obtains insurance eligibility information. The clerk must use one POS terminal to access data gateway 1, another POS terminal to access data gateway 2, etc. This further complicates the work of the admissions clerk, making it less likely that the clerk will timely provide insurance verification checks of incoming patient insurance coverage. Even when a programmed personal computer is used to replace several POS terminals, the clerk must know how to operate several different software packages corresponding to the different clearinghouses.

To add even further complication, health insurance eligibility is often not capable of being fully specified by a "yes" or a "no" answer. In the increasingly complicated world of health insurance, eligibility may involve qualifications, particular benefits packages, and other important additional information. For example, hospitals often need to know whether the hospital is a member of the patient's managed care group. In addition, the hospital may need to know about co-payment arrangements as well as the patient's previous health care services provided under a certain insurance coverage. These additional complications make eligibility verification more time consuming and difficult—making it even less likely that proper verification will be obtained at the time of patient admission.

Because of the various pressures involved in a health care provider admissions office (where the prime concern is usually to provide needed care to incoming patients as rapidly as possible), and because of the various complexities mentioned above, many hospitals have no reliable system or procedure for verifying that each incoming patient is actually eligible for the insurance coverage he or she asserts. Many times, health insurance coverage eligibility is not verified until after the patient has left the hospital or other health care provider, and the hospital or provider is attempting to collect payment for services rendered in the past. By this time, it may not be possible to locate the patient to obtain further information about his or her health care insurance. This results in great inefficiencies, wasted effort in attempting to collect from the wrong insurers, and loss of revenue and cost recovery to the health care providers.

The present invention provides method and apparatus for solving these and other problems.

The present invention provides a process that uses both hardware and software to capture print images from a health care provider computer system. The data from the print image is used to request real-time electronic insurance eligibility verification information from health care insurance payors. This electronic eligibility data is received directly from the payor, or through third party value added networks such as clearinghouses. Once the patient registration print image is captured, the print image is broken down into separate data fields. The data fields together represent information used to admit or register a patient into a health care provider facility. Each group of patient data is considered a separate transaction. The system provided by the present invention reviews the data items within each transaction to determine if the eligibility of the patient can be verified. The insurance carrier is determined for each transaction. On the basis of the insurance carrier, the system determines which electronic data source to request patient eligibility data from. The system reformats the transaction data to fit the data format required by the data source. The system initiates a telephone call via a modem to the data source. The system checks and confirms a clear data connection. The system sends the reformatted eligibility request transaction data to the data source. The data source sends to the system eligibility response data. The system then receives the patient specific eligibility response data, making sure that the transfer of data has occurred without data loss. The system then stores certain data elements from both the patient transaction and the eligibility data received. The system then prints out the data received from the data source on a printer connected to the local computer. The system then processes the next transaction, or waits to receive the next transaction.

Thus, in accordance with one aspect provided by the present invention, health patient insurance coverage is automatically verified by inputting, into an automated admissions computer system, information relating to a patient to be admitted to a health care provider. Based on this inputted information, the automated admissions computer system generates and sends digital signals to a printing device for printing a standard admissions document, such as an admission form. In accordance with one aspect of the present invention, this printed information is "intercepted" and certain patient related information is extracted from it. Then automatically, based on this extracted information, a digital insurance verification request message is generated. The digital insurance verification request message is communicated in real-time over a telecommunications link, and a digital insurance verification response message is received in real-time over the telecommunications link. This response message is used to verify patient insurance eligibility.

In accordance with another aspect of the present invention, information relating to a patient is automatically obtained from an admissions computer system. A digital verification request message is generated based at least in part on the obtained patient information. This digital verification request message is communicated to a verification institution, and a digital verification response message is received in response to the communicated digital verification request message. Based on the received verification response message, an indication of at least one aspect of the patient's health insurance coverage is provided to the patient's health care provider. These operations occur in real-time (preferably at the time the patient is admitted but, in any event, sometime prior to the time the patient is discharged from the health care provider).

The following are some of the advantageous features and advantages provided by the present invention:

The system provided by the present invention captures patient demographic and insurance information from the provider patient registration software system without requiring programming changes to that system. All other systems require significant changes to the providers system. In addition, the provider information system staff will have to be involved a great deal.

The system provided by the present invention can access and process eligibility transactions from an unlimited group of data sources.

The system provided by the present invention automatically reformats the patient data to the data set required by the eligibility data source to effect a transaction.

The system provided by the present invention uses the patient data to determine which data source to communicate with to obtain the insurance eligibility data for the transaction being processed.

The system provided by the present invention stores and emulates the individual communication protocols and transaction procedures for each source of insurance eligibility data.

The system provided by the present invention saves the transaction data to produce reports and provide usage information separate from the host health care provider system.

The system provided by the present invention requires no human interaction to process a transaction.

The system provided by the present invention contains subroutines which maintain the data structures and communication standards for each source of eligibility data. These subroutines can be updated via modem to add new sources of eligibility data.

The system provided by the present invention determines if the patient data set contains the proper data elements for the data source to respond to an eligibility request.

The system provided by the present invention tracks all processed transactions to provide data about usage for billing the provider and for monitoring of the system.

The system provided by the present invention saves personnel resources and time.

Because verification is automatic, verification is always obtained from the appropriate payor, even when multiple sources are involved.

Eliminates a lot of terminals, each dedicated to a gateway clearing house.

Eliminates need for redundant data entry and prevents associated errors.

No need to modify existing admissions software/hardware.

Can adapt to a large number of different admissions software/hardware systems.

Automatic real-time verification at "front end" of admissions process, before care is given.

Possible to interface with multiple (e.g., a large number) of payor sources.

Real-time insurance eligibility information allows health care provider to ask patient about alternate insurance/payment ability if asserted insurance eligibility is not verified.

BRIEF DESCRIPTION OF THE DRAWINGS

These and other features and advantages of the present invention may be better and more completely understood by referring to the following detailed description of a presently preferred exemplary embodiment in conjunction with the drawings, of which:

FIG. 8 is a flowchart of exemplary program control steps performed by a communication process provided by the present invention;

FIGS. 9A–9D are schematic illustrations of exemplary data structures provided by the present invention; and FIG. 10 is an illustration of an exemplary admissions form, the corresponding print stream of which is captured by the capture process shown in FIG. 7.

DETAILED DESCRIPTION OF THE PRESENTLY PREFERRED EXEMPLARY EMBODIMENT

Figure 1:
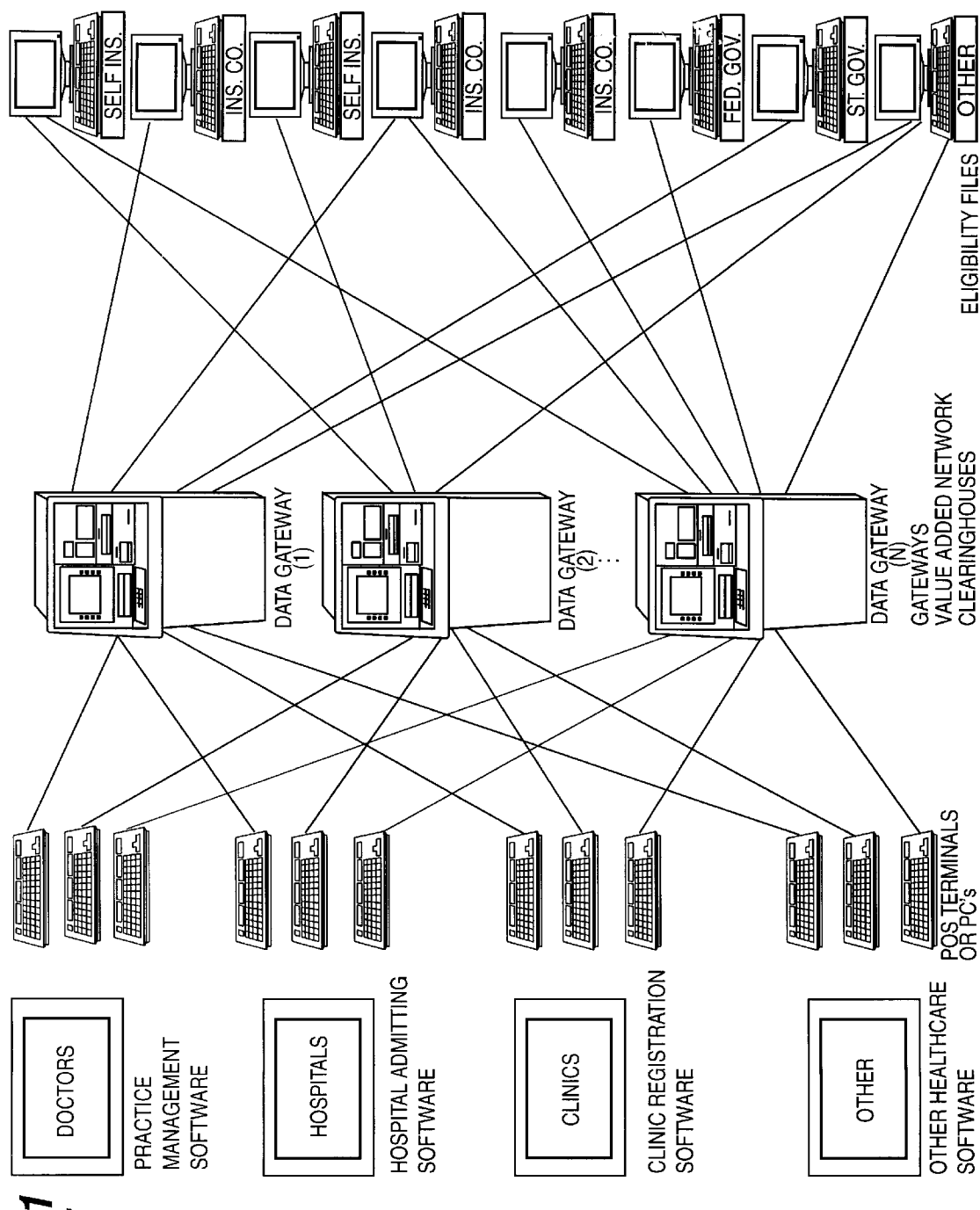
FIG. 1 is a schematic illustration of an exemplary prior art "network" for verifying insurance eligibility.
Figure 2:
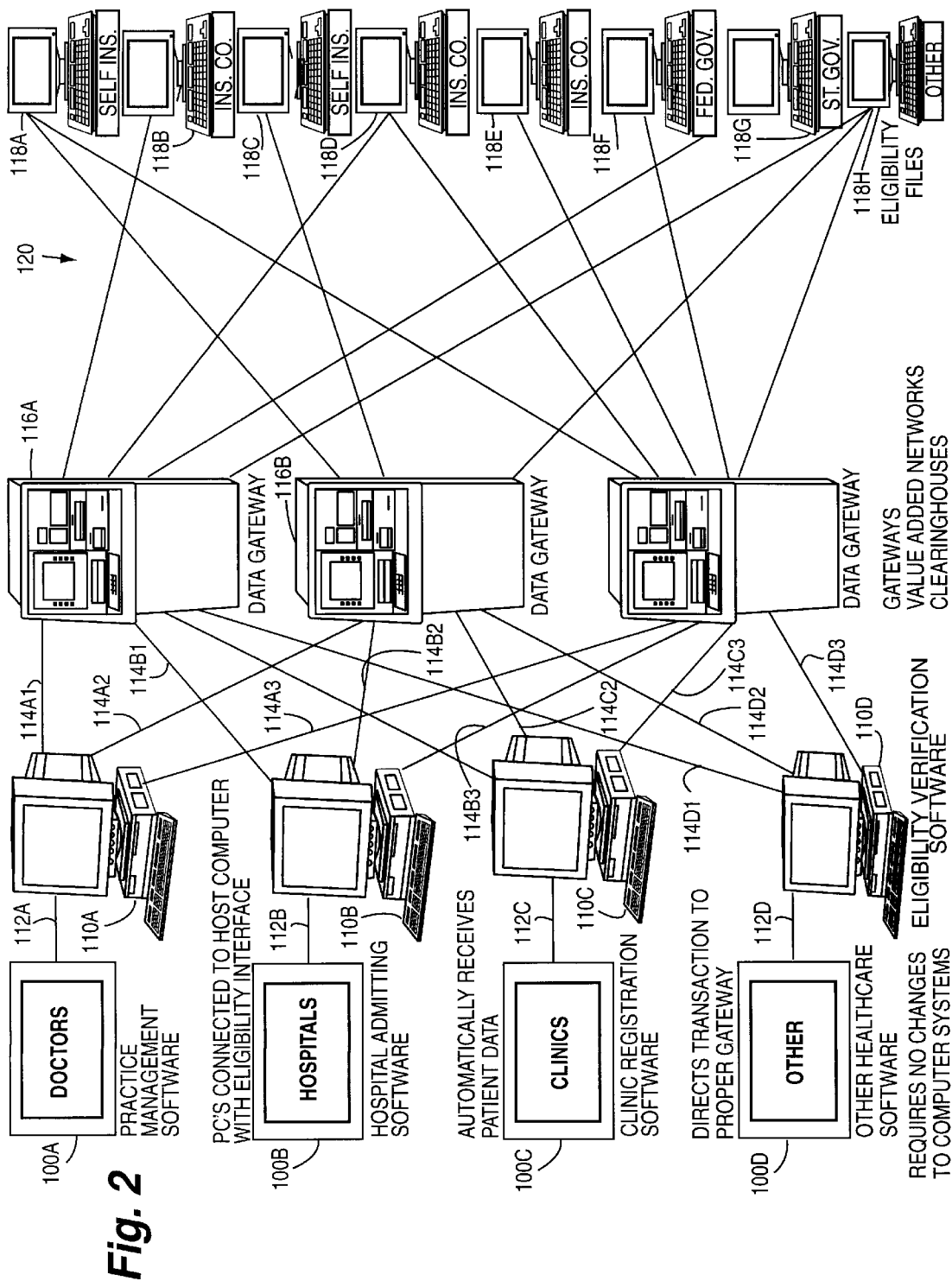
FIG. 2 is a schematic illustration of insurance eligibility verification as provided by the present invention.
Figure 10B:
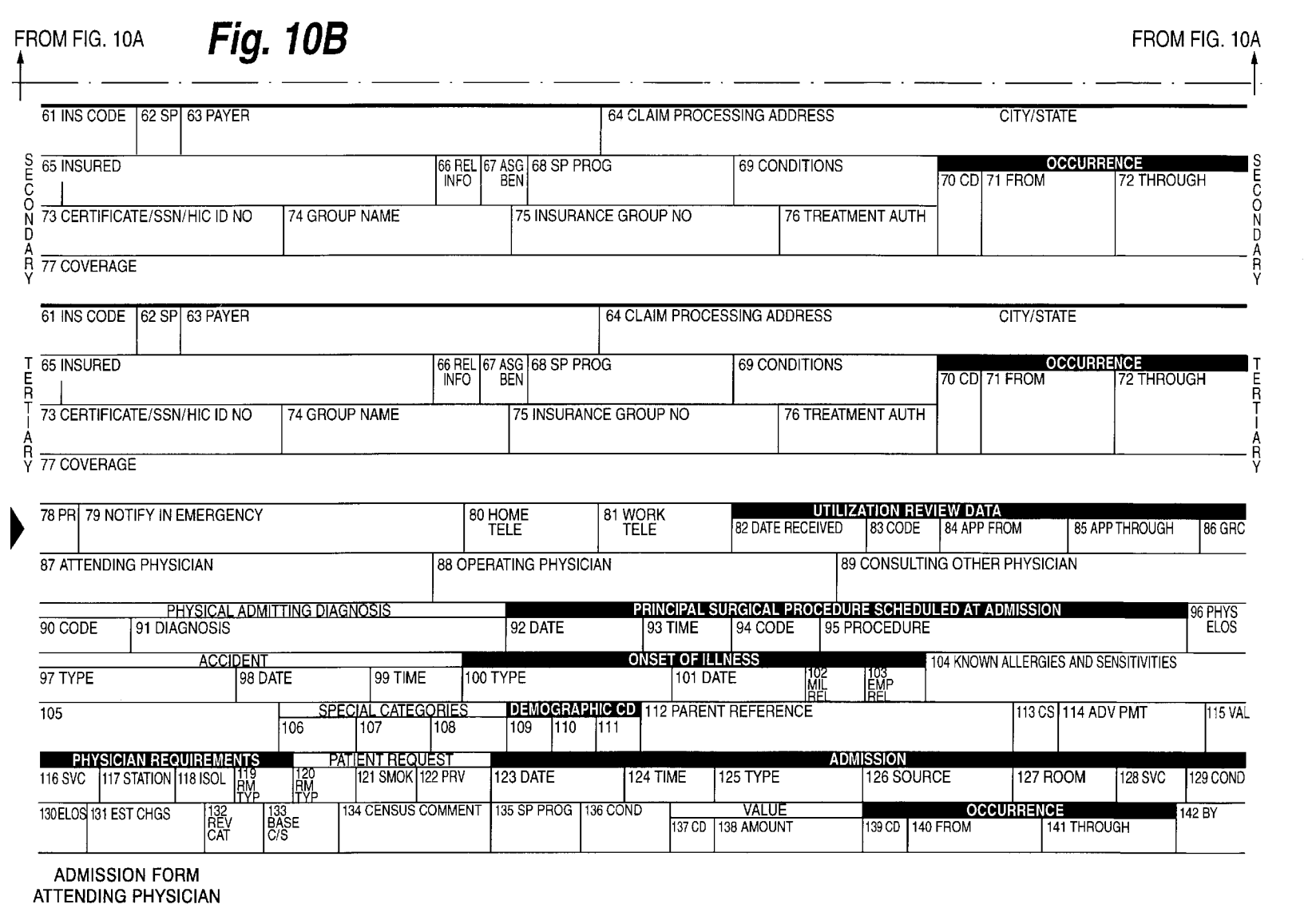

FIG. 2 is a schematic illustration of an exemplary real-time health insurance eligibility verification "network" provided by the presently preferred exemplary embodiment of the present invention. As shown in FIG. 2, various health care providers (e.g., doctors' offices 100A, hospitals 100B, clinics 100C, and other health care providers 100D) are each provided with a real-time eligibility verification system 110 and associated software. Each real-time eligibility verification system 110 is connected to the health care provider admissions computer system by link 112. In the preferred embodiment, personal computers 110 establish a link 114 on an as-needed basis with an appropriate one of data gateways 116 in order to obtain information regarding the eligibility of specific health care patients. Health care providers 100 input admission information regarding a particular health care patient into their respective admissions, practice management or other health care computer system. Generally, one of the outputs of such admissions process is a computerized admissions form (see FIG. 10 for an example) printed by a computer printer attached to the admissions system. In the preferred embodiment of the present invention, real-time eligibility verification system 110 intercepts and obtains a copy of the "print stream output" the admissions or other system sends to its local printer for printing over link 112. Real-time eligibility verification system 110 executes appropriate software in the preferred embodiment to analyze and extract data from this copy of the "print stream" it has captured from the admissions system. Based upon this extracted information, the real-time eligibility verification system 110 generates an associated file which it stores on local storage. This file contains information about a particular patient, including asserted health insurance eligibility information. Based on the contents of this file, real-time eligibility verification system 110 determines the appropriate data gateway 116 to contact in order to verify the patient's insurance eligibility.

Real-time eligibility verification system 110 establishes real-time telecommunications links 114 on an as-needed basis (e.g., via modem and telephone lines or other real-time telecommunications networks) with any of plural data gateways ("clearinghouses") 116. Data gateways 116, in turn, each have access to and provide information about insurance eligibility. This information is supplied to gateways 116 by one or more health care insurance payors 118. As can be seen from FIG. 2, different data gateways 116 may have access to different insurance payors 118. For example, data gateway 116A is the only one of the data gateways shown that has access to information about the eligibility rolls of insurance company 118B. The communications links 120 between data gateways 116 and insurance providers 118 may be real-time digital links but, more typically, may comprise a so-called "batch" type of information transfer (e.g., physical transfer of tape or other mass storage media from the insurance providers 118 to data gateway 116 containing current information about health insurance eligibility).

Real-time eligibility verification system 110 has routines that include the communications protocol for each of the plural data gateways 116 shown in FIG. 2 (although some standards work is ongoing in the health care industry, as of the present time, each of the many data gateways typically uses its own chosen data communications protocol, commands, response, etc.). Real-time eligibility verification system 110 determines the appropriate protocol and other information associated with the data gateway 116 from which it will access insurance eligibility information pertaining to this particular patient, and establishes a real-time communications link 120 with the appropriate data gateway 116 (e.g., via modem over a telephone line). Real-time eligibility verification system 110 sends an eligibility request message in real-time to the data gateway 116, and obtains and captures a response from the data gateway over link 114. Real-time eligibility verification system 110 then analyzes the response message for desired eligibility information, and may provide an indication of patient eligibility (e.g., by printing an eligibility report, displaying eligibility information on a CRT, etc.).

Figure 3:
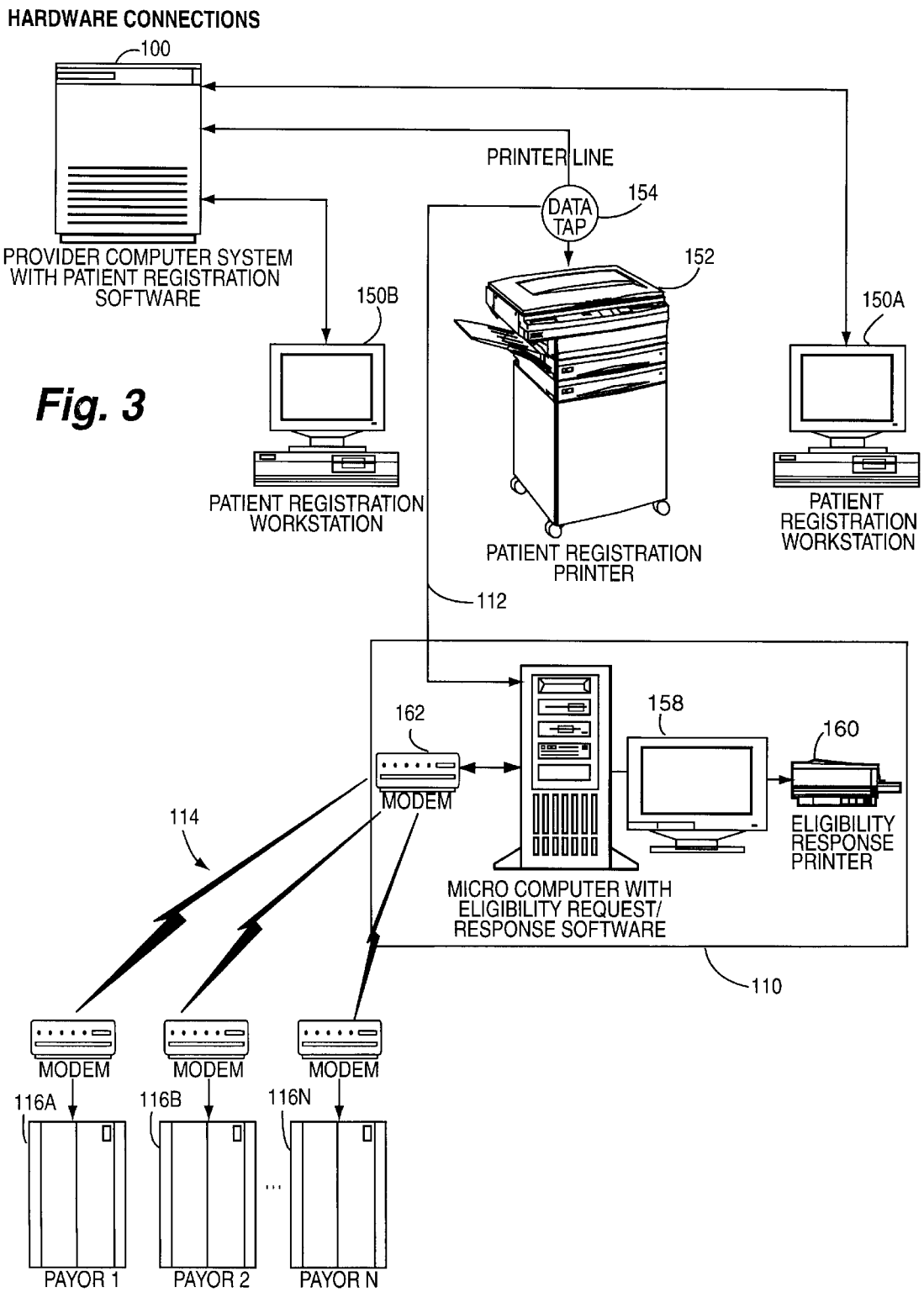
FIG. 3 is a block diagram of exemplary system architecture provided by the presently preferred exemplary embodiment of the present invention.

FIG. 3 is a schematic illustration of an exemplary architecture of the presently preferred exemplary embodiment provided by the present invention. An exemplary provider computer system 100 is shown at the upper left-hand corner of the page. This provider computer system 100 typically has one or more patient registration workstations 150 connected to it, as well as a patient registration printer 152. An admissions clerk interviews a patient prior to admitting the patient to the hospital, for example, and inputs the information resulting from the interview into provider computer system 100 via patient registration workstation 150. Based upon this inputted information, provider computer system 100 prints an admissions form (see FIG. 10 for an example). The admissions form is often attached to the patient's "chart," and is otherwise used for processing by the hospital. In accordance with one aspect of the present invention, a "data tap" 154 is connected between the provider computer system 100 and the patient registration printer 152. Data tap 154 does not prevent the print stream data generated by provider computer system 100 from getting to patient registration printer 152, but it does allow real-time eligibility verification system 110 to "listen in" to the print stream. Data tap 154 may comprise, for example, a conventional passive "splitter" for making a "Y" connection in a standard RS-232 serial line.

Real-time eligibility verification system 110 in the preferred embodiment includes a main unit 156, a display device 158, an eligibility response printer 160, and a modem 162. As mentioned above, main unit 156 may be connected to data tap 154 via a conventional RS-232 serial port. Similarly, main unit 156 may be connected to modem 162 via a conventional serial port, and is also connected to eligibility response printer 160 in a conventional fashion. Main unit 156 receives print stream information from provider computer system 100 via data tap 154, and stores the print stream information on an internal hard disk or other associated storage device. Main unit 156 performs these functions under program control. Other program control allows main unit 156 to extract information from the captured print stream data, and initiate a real-time contact with a data gateway 116 via modem 162. Although only one modem 162 is shown, it will be understood by those skilled in the art that multiple modems may be provided as part of real-time eligibility verification system 110 so that multiple simultaneous communication links 114 may be established. Main unit 156 transmits appropriate eligibility request messages to data gateways 116 via real-time communication links 114, and receives real-time responses. Based upon these responses, main unit 156 may provide indications of insurance eligibility on display 158, and/or may print eligibility reports on printer 160. In addition, main unit 156 keeps track of the number of insurance eligibility transactions it has performed. This record-keeping allows the owner/operator of real-time eligibility verification system 110 (which may be leased to the hospital or other health care provider) to receive compensation based on the number of eligibility transactions performed.

Figure 4:
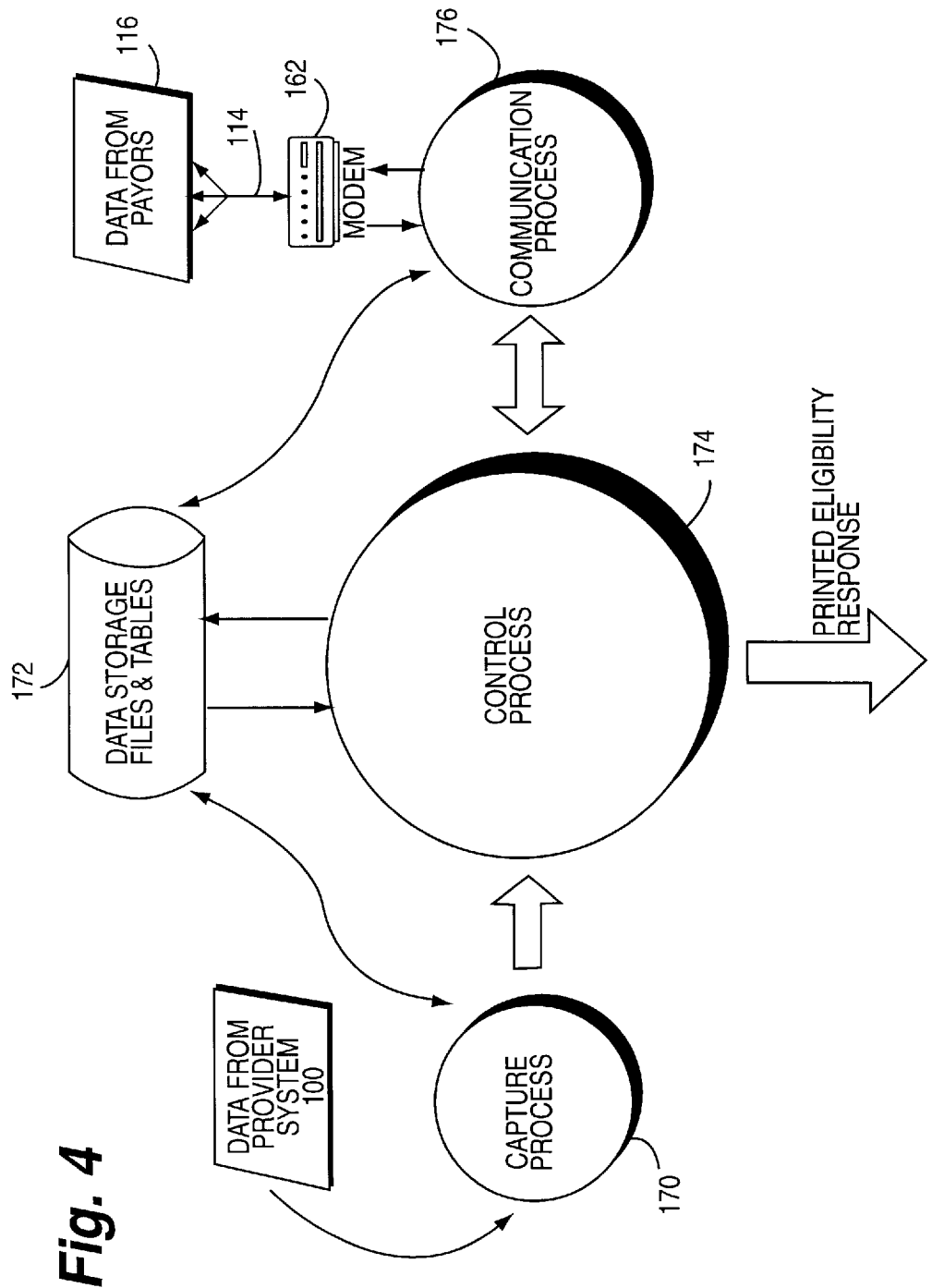
FIG. 4 is a high level schematic illustration of the various high level processes performed in accordance with the presently preferred exemplary embodiment of the present invention.

FIG. 4 is a schematic illustration of the three high-level processes performed by real-time eligibility verification system 110 under program control in the preferred embodiment. Data from provider computer system 100 is inputted to a capture process 170 which acts to capture the information and store it on a storage device 172. The capture process 170 also informs a control process 174 that the information has been captured and stored. The control process, in turn, retrieves the captured information from data storage 172, extracts appropriate information, and passes the extracted information to a communications process 176. Communications process 176 controls modem 162 to establish a real-time communications link 114 with a clearinghouse or other insurance payor 116. Communications process 176 sends eligibility request messages in the appropriate protocol and other format over communications link 114, and receives real-time responses from payor 116 via the link. Communications process 176 may store received response information on storage device 176, and inform control process 174 that information has been received. Control process 174 in the preferred embodiment then retrieves and analyzes the response messages received by the communications process 176, and outputs an indication of insurance eligibility (e.g., on display 158 and/or printer 160).

Figure 5:
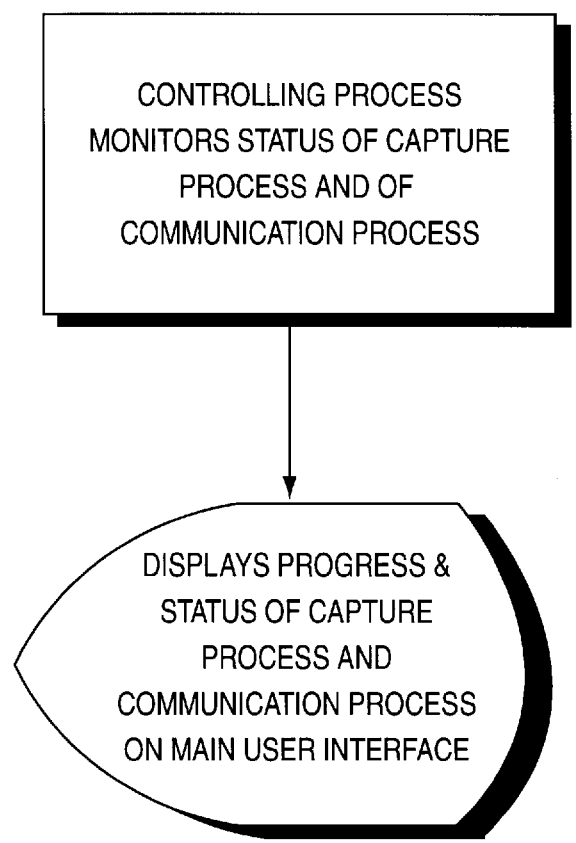
FIG. 5 is a flowchart of exemplary interaction between a control process, a capture process and a communication process provided by the preferred embodiment of the present invention.

In the preferred embodiment, main unit 156 executes a "multi-task" operating system such as MICROSOFT WINDOWS®. Thus, in the preferred embodiment the capture process 170, the control process 174 and the communications process 176 all operate concurrently. FIG. 5 shows portions of the control process 174 which interact with the capture process 170 and the communications process 176. Thus, FIG. 5 shows that the control process 174 monitors the status of the capture process 170, and displays progress and status of capture process and communications process on display 158.

Figure 6:
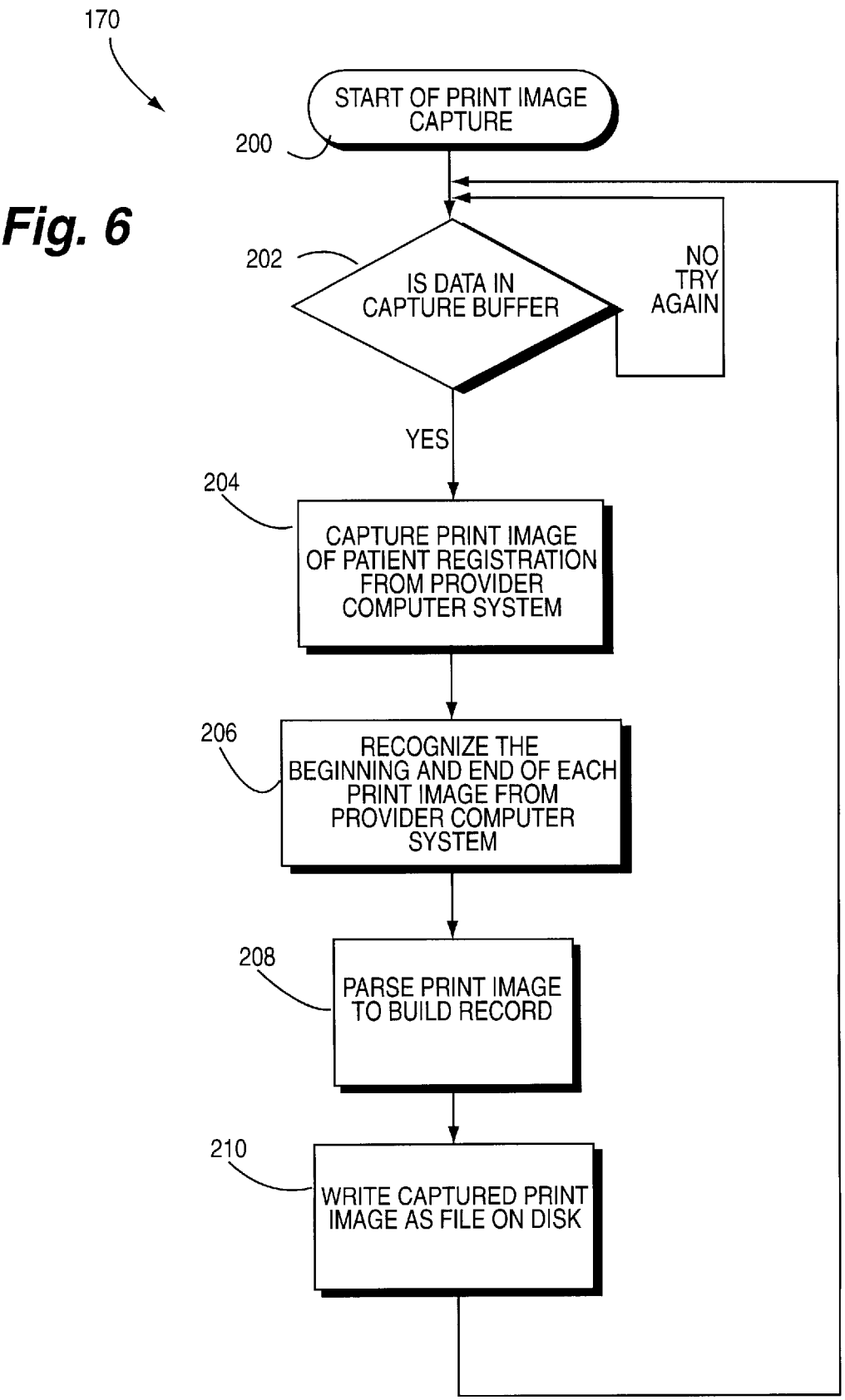
FIG. 6 is a flowchart of exemplary program control steps performed by a capture process provided by the preferred embodiment of the present invention.

FIG. 6 is a flowchart of exemplary program control steps performed by the preferred embodiment capture process 170. Capture process 170 operates as a continual loop. Once started by the operating system (bubble 200), the capture process 170 determines whether there is data in the capture buffer (block 202). As will be understood by those skilled in the art, capture process 170 maintains a buffer which is used in connection with an "interrupt handler" to obtain and temporarily store characters received on the serial port from data tap 154. Decision block 202 is repeated until data is detected in the capture buffer ("yes" exit to decision block 202). Once captured data is detected, capture process 170 captures the entire print image of the patient registration form (see FIG. 10) from provider computer system 100, and stores the captured print image in the computer's memory (RAM) (block 204). Capture process 170 then analyzes the received print image (e.g., by searching for predetermined characters introduced into the beginning and ending of the print stream by provider computer system 100) in order to isolate the beginning and end of each print image (block 206). As will be understood by those skilled in the art, the specific characters block 206 searches for will depend upon the particular type of computer used as provider computer system 100, the particular type of printer 152 used to print patient admission registration forms, and possibly other variables. This information is customized into main unit 156 for each installation of real-time eligibility verification system 110. Once capture process 170 has isolated a print image, it parses the print image and builds a data record (block 208) which it then writes onto mass storage 172 (block 210). Capture process 170 then returns to decision block 202 to await receipt of the next print image from provider computer system 100.

FIGS. 7A–7G together are a flowchart of program control steps performed by control process 174 in the preferred embodiment. When control process 174 is started (block 250), it first determines whether there are any print images stored on data storage 172 by capture process 170 that have not yet been processed. If such as-yet-unprocessed print images exist, control process 174 retrieves a print image from data storage 172 (block 252), and parses the print image for data elements based upon the location of the specific data elements within the print image (block 254). As will be understood by referring to FIG. 10, certain information (e.g., the patient's legal name, the patient's birth date, the patient's medical record number, the name of the responsible party, the name of the payor, insurance group number and name, etc.) are contained within the print image captured by the capture process 170. Block 254 extracts the relevant information from the captured print image file. As will be understood by those skilled in the art, the specific places in which the block 254 looks for information to extract will change from one installation to another because different provider computer systems 100 are configured differently and use different software, standard print forms, etc. Thus, the operation of block 254 is preferably customized in the preferred embodiment for the specific provider computer system 100 on an installation-by-installation basis.

Control process 174 next chooses, from the parsed data elements, those data elements necessary to perform an eligibility transaction (block 256). This may involve choosing some specific data elements because of their relationship with other data elements. For example, if the patient being admitted is a minor, it may be that the insurance is in the name of a parent. Requesting insurance eligibility verification in the name of the child may provide a negative eligibility response, whereas requesting the eligibility information in the name of the "responsible party" information on the admission form may provide the desired eligibility verification. Block 256 thus attempts to choose, from the various information inputted, the appropriate information for verifying insurance eligibility. As will be understood, the rules applied by block 256 to choose appropriate data elements will often vary from one installation to the next based on provider computer 100 configuration, provider computer software, and/or the practices followed by the admissions clerks in entering information into the provider computer system. Thus, these rules are typically customized for the particular installation system 110 is being installed in.

Once the data elements have been chosen from the print image by block 256, they are tested for validity (block 258). If appropriate data is not present in specific data fields ("no" exit of decision block 260), the print image is discarded (block 262), and control returns to block 252 to retrieve the next print image from disk. If, on the other hand, data is present in the specific data fields ("yes" exit of decision block 260), then control proceeds to block 264 (see FIG. 7B) where the billing number and the extracted data (or other appropriate indicia) is compared with existing billing numbers in a history transaction request table (not shown). In the preferred embodiment, system 110 maintains a log file containing, for example, billing numbers of all transactions that have occurred within the past certain time period. The comparison performed by block 264, decision block 266 ensures that redundant eligibility verification is not being performed (i.e., if insurance eligibility verification has recently been performed for this particular billing transaction, there is no need to re-verify eligibility). If the billing number of the newly received admissions transaction matches the billing number in the transaction request table ("yes" exit to decision block 266), then control routine 174 compares the new request with the previous request (by referencing more complete information about past requests that may be stored on mass storage device 172) (block 268). If the new request data is identical to previous requested information ("yes" exit to decision block 270), then no eligibility verification is necessary (eligibility has already been recently determined) and control returns to block 252 shown in FIG. 7A (block 272). If the new request is not identical to the prior requested data ("no" exit to decision block 270), then the transaction request table is updated with the new data and certain request flags are set to request the communications process 176 to generate an eligibility request (block 274). If the new billing number does not match the billing number in the transaction request table ("no" exit of decision block 266), then request information is added to a transaction request table so that a new request will be generated by communications process 176 (block 276).

FIG. 9B is a schematic illustration of an exemplary format for a transaction request table provided by the preferred embodiment of the present invention. Transaction request table 400 includes the following fields:
Patient request ID 400
Patient middle initial 402
Patient last name 406
Patient suffix name 408
Relation code 410
Billing number 412
Patient number 414
Patient date of birth 416
Patient sex 418
Benefit code 420
From date 422
To date 424
Insured first name 426
Insured middle initial 428
Insured last name 430
Insured suffix name 432
Insured SSN 434
Insured member ID 436
Insured ID 438
Insured employer name 440
Insured employer group 442
Provider network number 444
Payor ID 446
Payor name on form 448
Time added 450
Time request initiated 452
Time request completed 454
Response count 456
Lookup code 458
Network ID 460
Mail box flag 462
Request file name 464
Try count 466

This information is used by control process 174 to generate a real-time eligibility request and is also used by control process 174 to keep track of the current status of the request. Most or all of fields 400–440 contain information extracted from the print image received from the health provider computer 100. Fields 450–466, on the other hand, contain status information used by system 110 to keep track of the status of the current request. Once block 276 adds a request to the transaction request table, control continues to block 278 (see FIG. 7C) to communicate request information to the communications process.

Figure 7A:
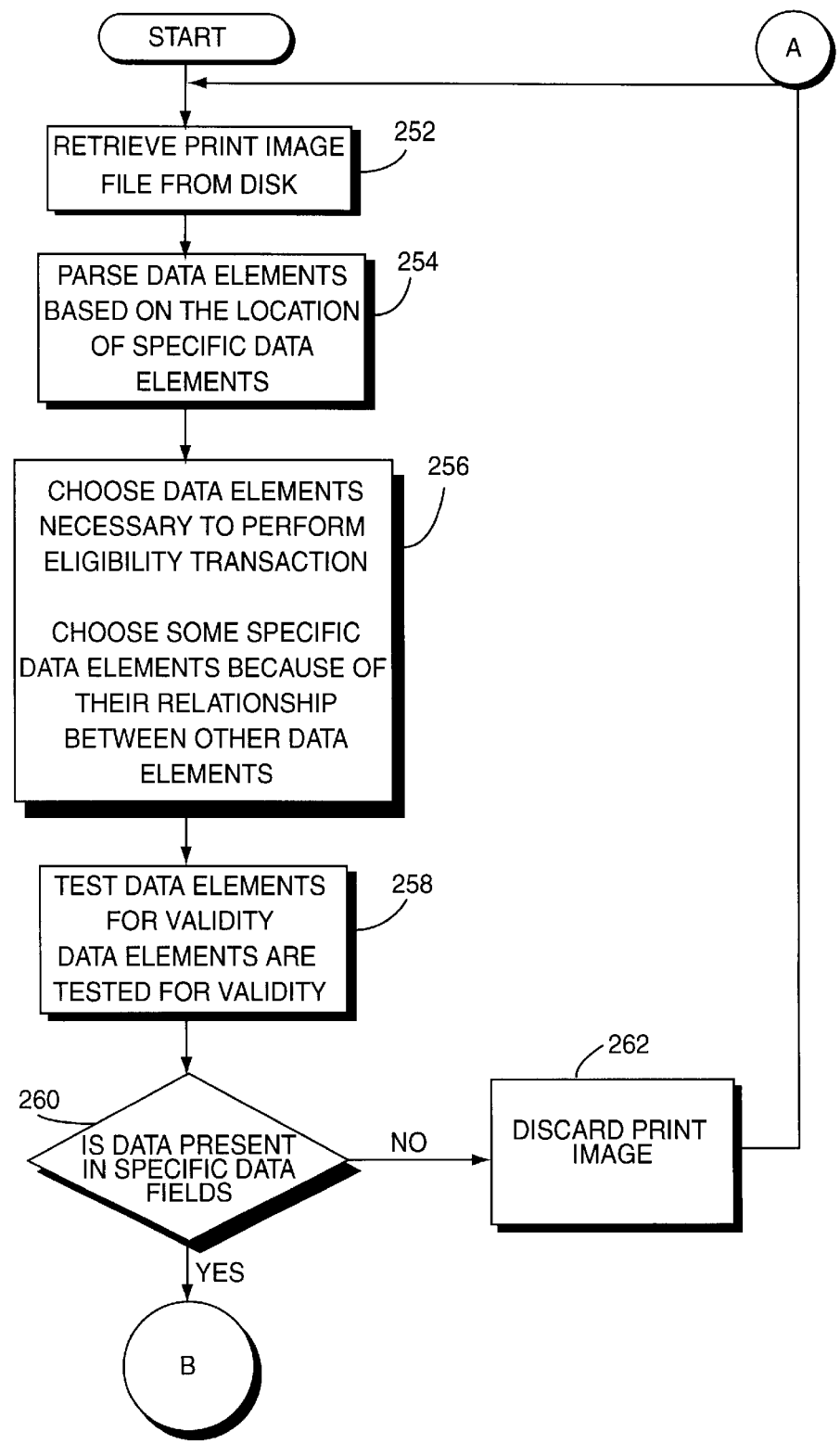
FIGS. 7A–7G together are a flowchart of exemplary program control steps performed by the control process provided by the preferred embodiment of the present invention.
Figure 7B:
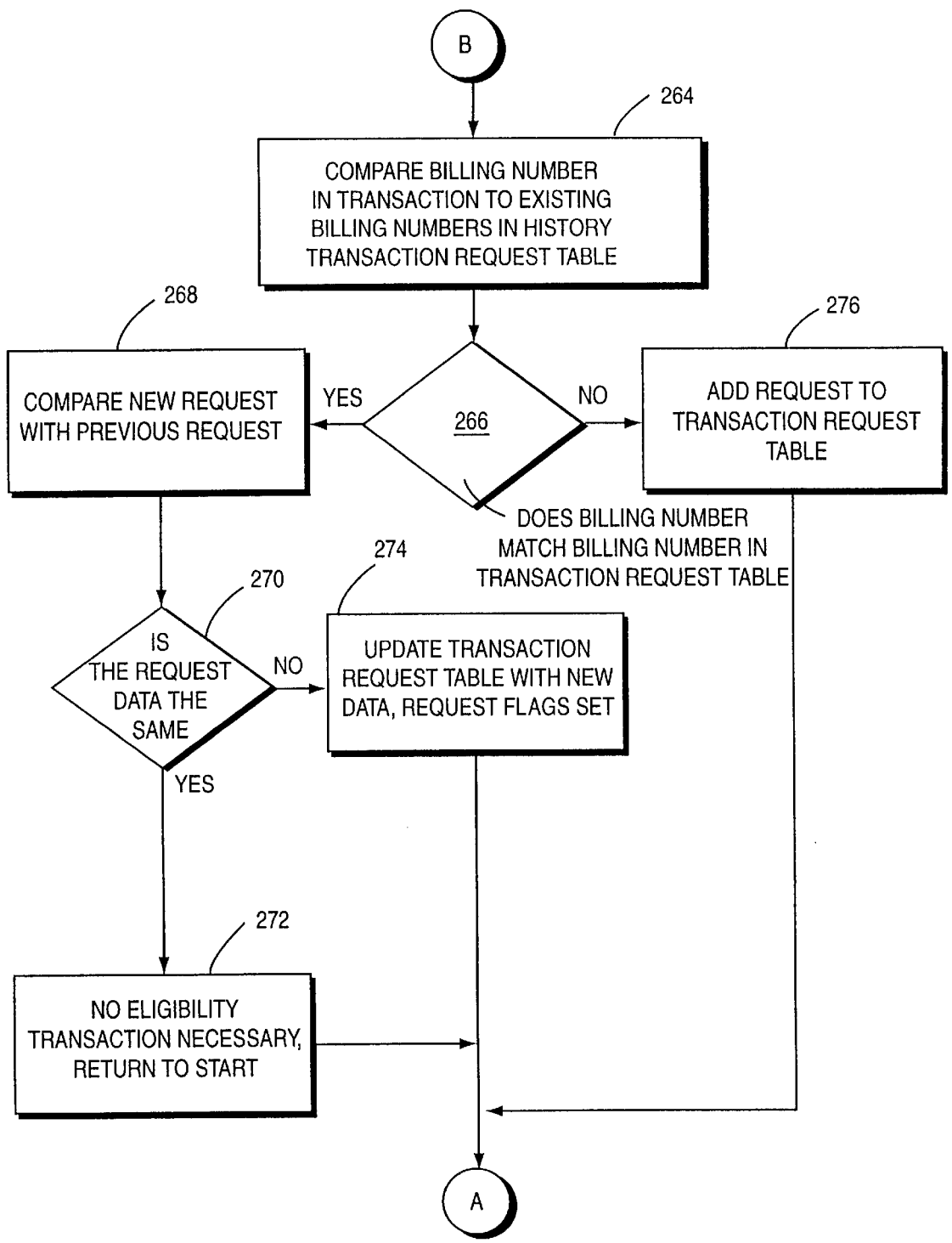
Figure 7C:
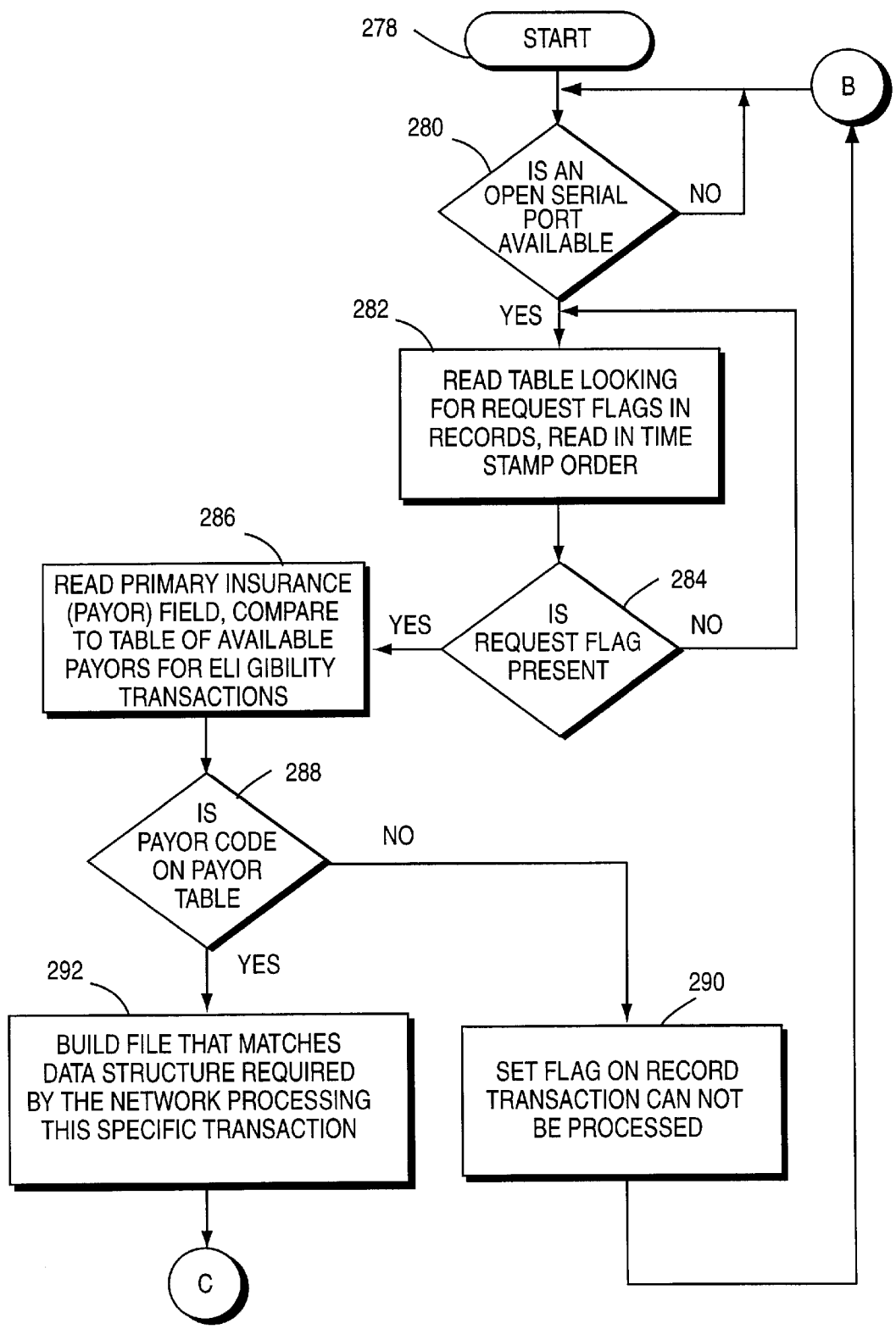
Figure 7D:
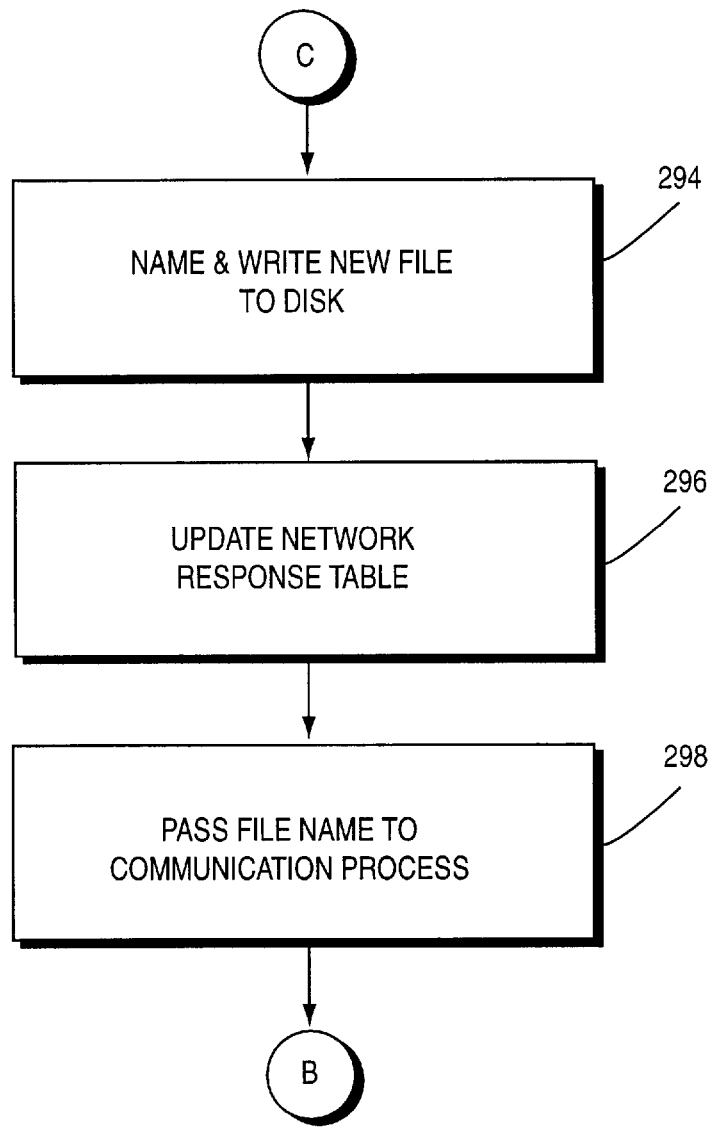

FIG. 7C is a flowchart of the portion of control process 174 that communicates request information to communication process 176. Upon starting the routine shown in FIG. 7C (block 278), system 110 first determines whether an open serial (modem) port is available (decision block 280). If a modem 162 is available, then the routine reads the transaction request table 400 to determine whether there are any request transactions that need to be handled (block 282). If the routine finds an entry in the transaction request table including a request flag set, such as in the "time request initiated" field (decision block 284), then the routine shown in FIG. 7C reads the primary insurance (payor) field 446 and compares to a table listing available payors for eligibility transactions (block 286, decision block 288).

Figure 9A:
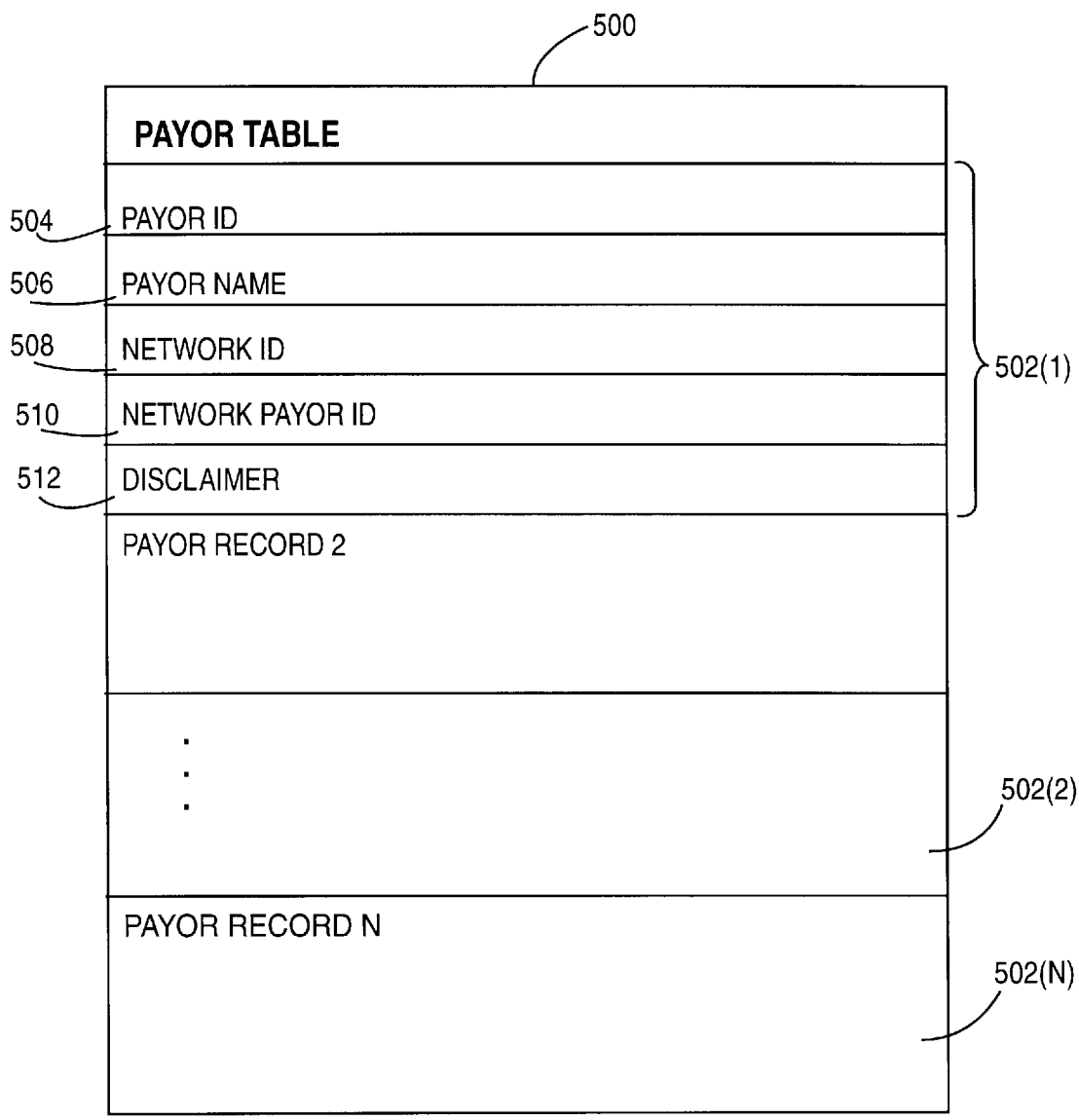

FIG. 9A shows an exemplary format for payor table 500 in a preferred embodiment. Payor table 500 in the preferred embodiment includes a plurality of payor records 502(1), 502(2), . . . 502(N), each payor record corresponding to a different payor. Each payor record 502, in turn, includes a payor ID field 504, a payor name field 506, a network ID field 508, a network payor ID field 510, and a disclaimer field 512. Decision block 288 determines whether any payor record 502 corresponds to the listed payor information in the newly captured print image. If there is no such match ("no" exit to decision block 288), then a flag is set in the transaction request table 400 indicating that the transaction cannot be processed (block 290), and control returns to decision block 280 to determine whether a serial port is still available for the next transaction. If, on the other hand, there is a match between a payor code in the new transaction and an entry in the payor table 500 ("yes" exit to decision block 288), then the FIG. 7C routine builds a file that matches the data structure required by the network (e.g., data gateway 116) processing this specific transaction (block 292). More specifically, the appropriate record 502 in the payor table 500 is accessed to determine network ID, and this network ID field 508 contents is used to access the appropriate routines for building an eligibility request for the specified network. These routines build a file that includes information specific to the eligibility transaction to be performed. This new file is then written to mass storage device 172 (block 294), and a network response table is updated (block 296).

Figure 9C:
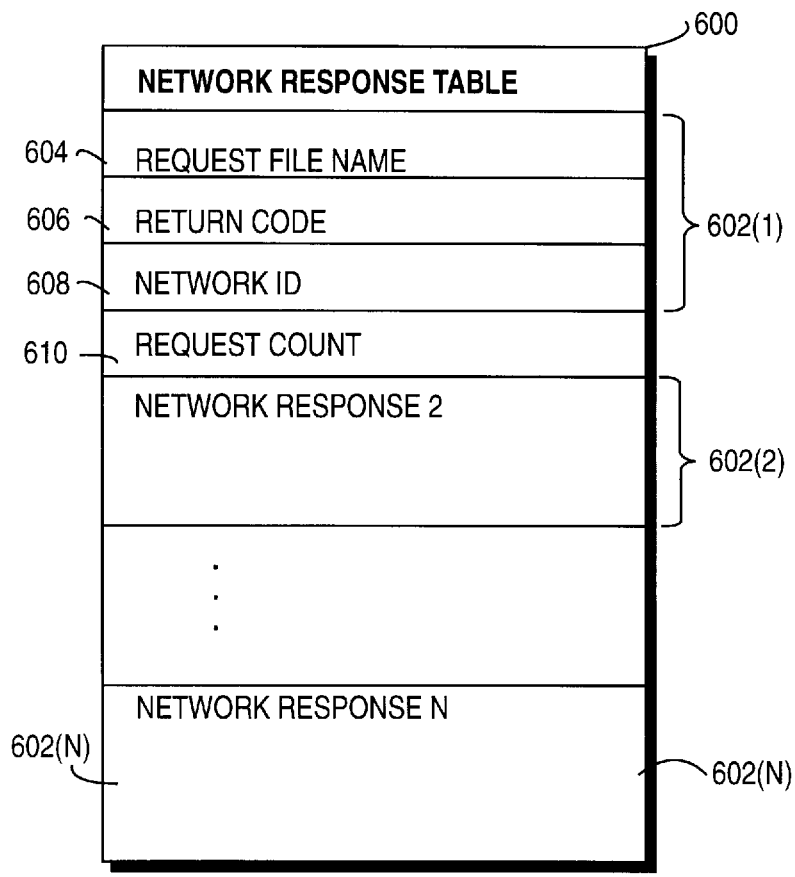

FIG. 9C shows an exemplary data format for the preferred embodiment network response table 600. In the preferred embodiment, network response table 600 includes a plurality of network response records 602(1), 602(2), . . . 602(N). Each network response record, in turn, includes a request file name field 604, return code 606, the network ID field 608, and the request count field 610. The request file name specifies the name of the request file written to disk by block 294. Once the network response table record 602 has been built, the file name or other designation of the corresponding request file is passed to communications process 176 (block 298), and control is then returned to FIG. 7C block 280 to handle the next request.

FIG. 8 is a flowchart of exemplary program control steps performed by the communications process 176 in the preferred embodiment. Upon starting the communications process 176 (block 300), the communications process opens a communications link 114 via modem 162 with the appropriate payor network (data gateway 116) by, for example, dialing the appropriate telephone number with the modem and establishing a real-time on-line connection (block 302). This connection is established by emulating the communications specification specific to the data gateway 116 being contacted based on the contents of the request file and the network ID field contents 608. Communications process 176 then transmits the network request file to the data gateway 116 (block 304), and "stays on the line" waiting for a response from the payor network (block 306). When the data gateway 116 transmits a response, communications process 176 receives the response and writes it to the mass storage device 172 (block 308. Communications process 176 then sends a return code ("return code 606," FIG. 9C) to the control process 174 (block 310) via a conventional DDE link and the communications process 176 ends (block 312).

Figure 7E:
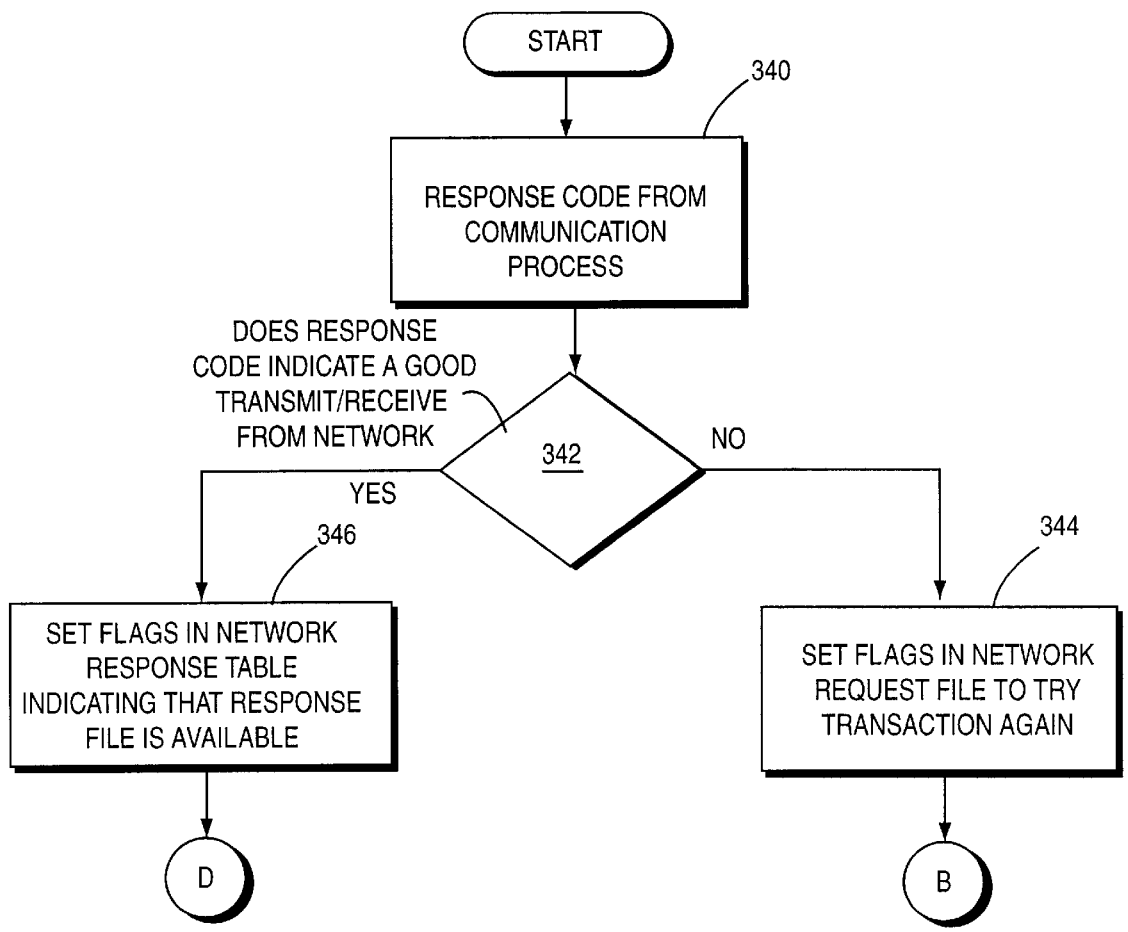

Referring now to FIG. 7E, an exemplary flowchart of a further portion of the control process 174, control process receives the code passed to it from the communications process block 310 (block 340), and tests on an interrupt basis whether the response code that has been received is acceptable (block 342). If the response is not acceptable, the control process sets flags in the network response table 600 to try the eligibility request again (block 344), and control returns to where it was when the interrupt began. If, on the other hand, the received response codes are acceptable ("yes" exit from decision block 342), then the control process sets flags indicating that the response file is available (block 346).

Figure 7F:
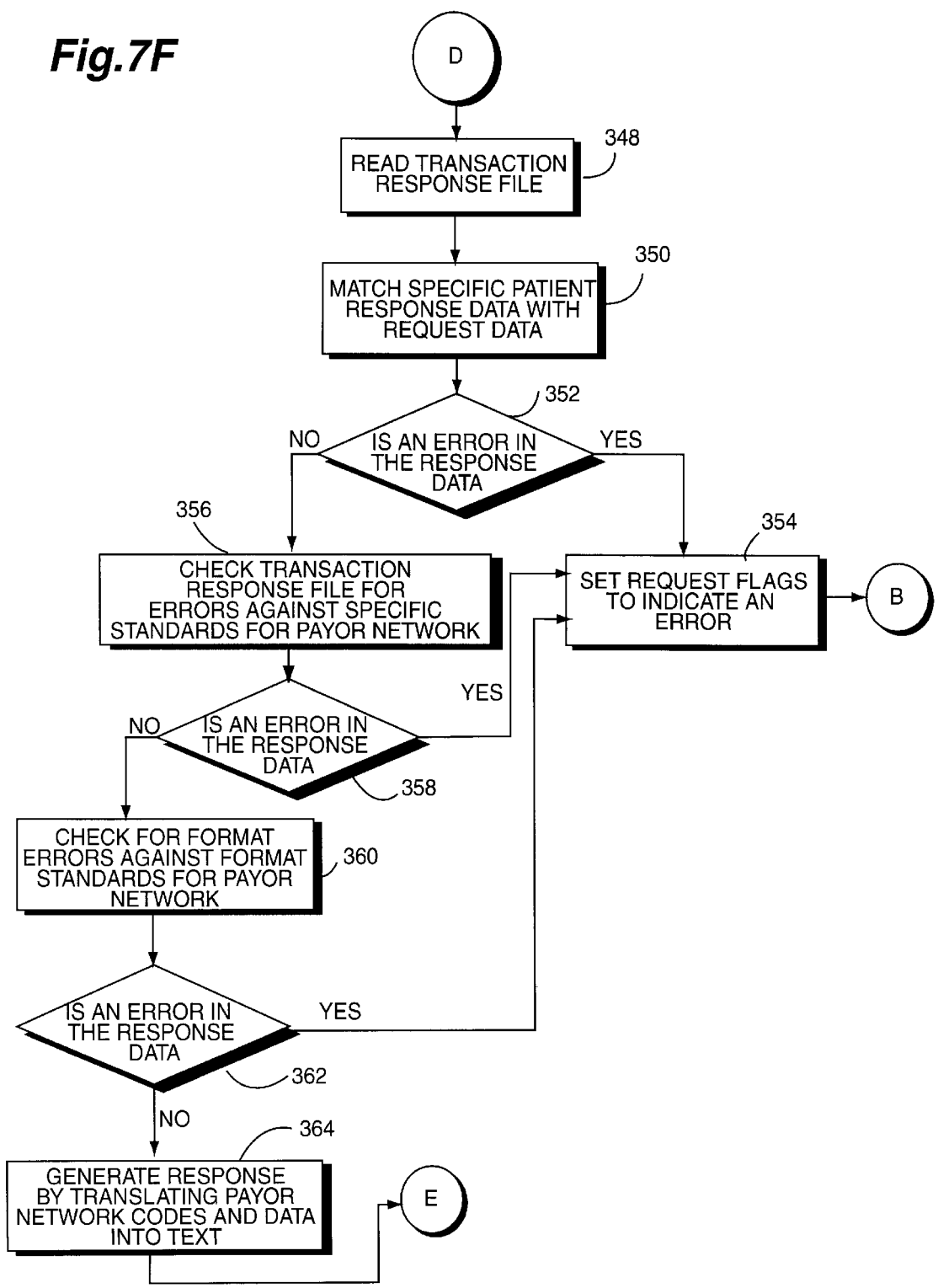
Figure 7G:
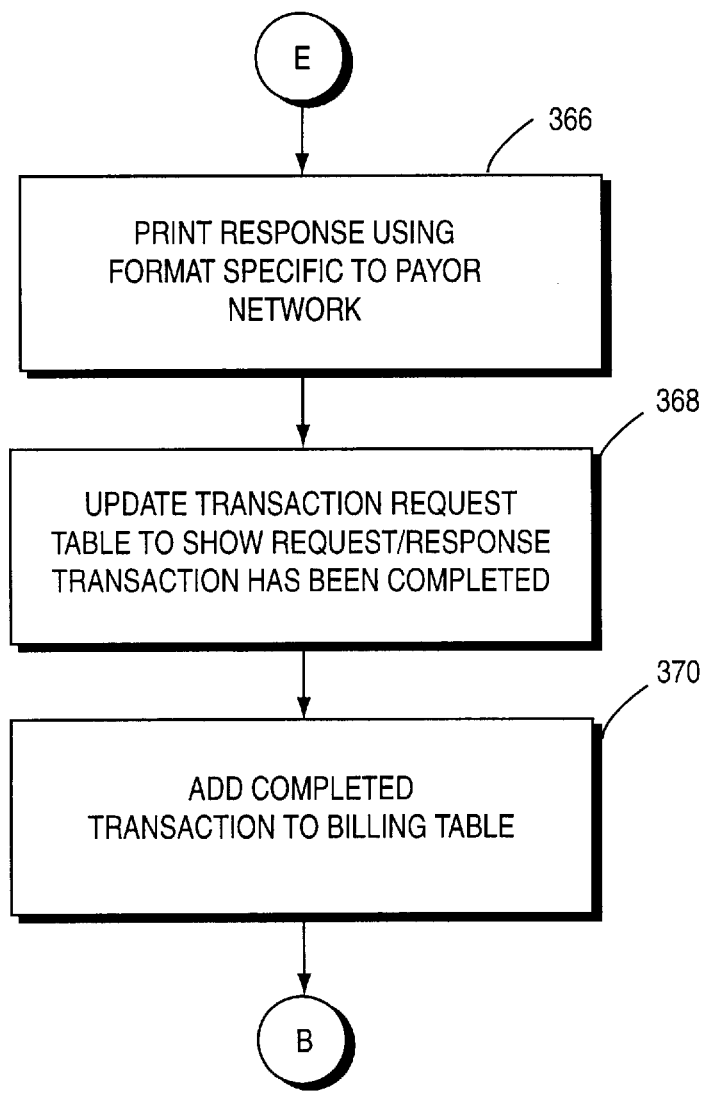

Referring now to FIG. 7F, the control process 174 next reads the transaction response file (block 348), and matches specific patient response data with request data (block 350). The structure of the transaction response file will depend on the network in which the system operates. Thus, block 350 matches insurance eligibility information obtained from the appropriate data in gateway 116 with patient-specific information stored within the transaction request table 400. If there is an error such that the information does not match (decision block 352), request flags are set to indicate an error (block 354), and control returns to FIG. 7A block 252. If there is no error ("no" exit to decision block 352), then control process 174 checks the transaction response file for errors against specific standards relating to the particular payor network (block 356). Once again, if there is an error detected in the received response, an error flag is set and control returns to another part of the control process 174 (decision block 358, block 354). Additional errors are checked for by comparing the format of the received response message against format standards for the particular data gateway 116 (block 360), and any errors generate an error indication (block 362, block 354). Assuming that all of the error tests (block 352, 358, 362) pass, then control process 174 generates a response by translating payor network codes and data into text (block 364). Such translation performed by block 364 is performed based upon specific dictionaries stored on mass storage device 172, for example, associating particular data gateway response codes with standardized text and other information used by system 110. System 110 then prints a response about eligibility using printer 160 and/or displays eligibility response indications using display 158 (block 366). Control process 174 next updates the transaction request table 400 entry to show that the request/response transaction has been completed (e.g., by writing appropriate information into field 454 and 458) (block 368). Finally, control process 174 adds the completed transaction information to billing table 700 shown in FIG. 9D (block 370), after which control returns to FIG. 7A block 252.

Figure 9D:
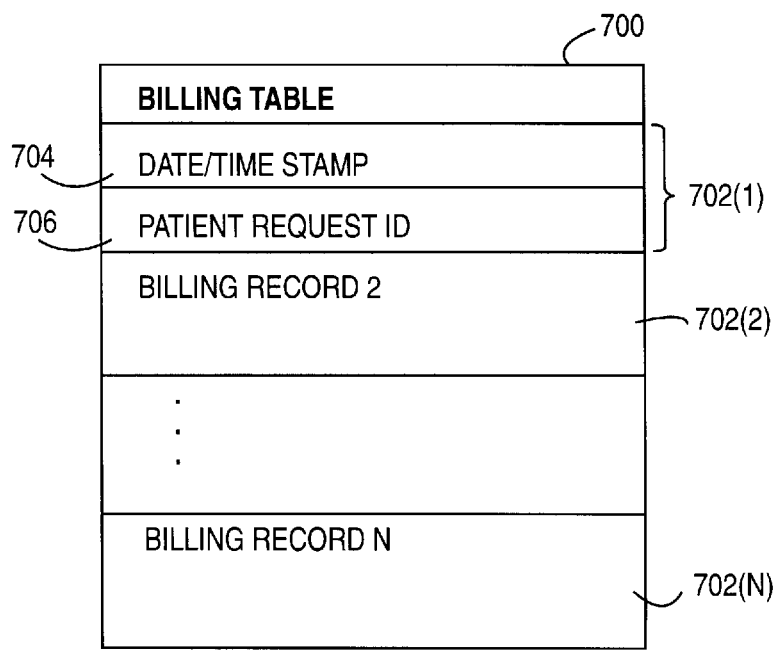

Referring to FIG. 9D, billing table 700 includes a plurality of billing records 702(1), 702(2), . . . 702(N). Each billing record 702 includes a date/time stamp field 704, and a patient request ID field 706. Billing table 700 is updated in the preferred embodiment each time an eligibility verification transaction has been completed. Billing table 700 may thus be used to track completed eligibility transactions, and in the preferred embodiment is also used to keep track of the compensation owed to the owner/operator of system 110. In accordance with this aspect of the present invention, eligibility verification system 110 is not sold to the health care provider, but rather is loaned or leased to the health care provider by a third party. The third party receives compensation for each eligibility transaction that computer system 110 completes for the health care provider. Billing table 700 thus maintains the "meter" information needed to determine the compensation that the health care provider owes to the owner of system 110.

A new insurance eligibility system has been described which is capable of automatically verifying insurance eligibility in real-time without requiring redundant data entry and without requiring modification of a health care provider admissions computer system. The preferred embodiment of the present invention replaces the multiple terminals of various payors, and inter-connects easily with existing health care provider admissions software and hardware without requiring modification thereof. Thus, hospitals and other health care providers which have invested much time, money and effort in developing, learning and maintaining a complicated computer admissions system do not need to modify their existing system in order to provide automatic insurance verification. In addition, the preferred embodiment of the present invention eliminates the need for any information to be entered both into the admissions system and into an additional computer or other device used to obtain eligibility information—since the information inputted into the admissions system is automatically captured and used for eligibility verification in real-time. Because the eligibility verification is automatic, it is performed without fail, irrespective of how busy the admissions clerk is at the time. Moreover, no additional or special training of admissions personnel is required for eligibility verification—since admissions personnel need only perform the steps they are used to performing for normal admissions procedures, and the eligibility verification is performed automatically without any additional human intervention being necessary.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. In a medical facility that utilizes an existing computerized healthcare patient registration computer system to input patient information and register patients for healthcare services, the existing computerized healthcare patient registration computer system lacking the capability to reliably verify patient health insurance coverage information in real time, the existing computerized healthcare patient registration computer system generating a digital output stream based at least in part on patient information inputted into the computerized healthcare patient registration computer system, the digital output stream including declared insurance provider information, a method of automatically, without requiring direct human intervention, verifying patient health insurance information using a patient health insurance verification computer system operatively connected to the existing computerized healthcare patient registration computer system, the method comprising the following steps:

(a) inputting, into the computerized healthcare patient registration computer system, information relating to a patient to be registered with a health care provider;

(b) based at least in part on said information inputted by the inputting step (a), generating a digital output stream with the computerized healthcare patient registration computer system and sending the digital output stream to an output device connected as part of the computerized healthcare patient registration computer system;

(c) capturing, with the patient health insurance verification computer system operatively connected to the computerized healthcare patient registration computer system, the digital output stream the computerized healthcare patient registration computer system generates in step (b), and extracting at least some patient related information including said declared insurance provider information from said digital output stream;

(d) generating, with the patient health insurance verification computer system, a digital insurance verification request message that is formatted based at least in part on said extracted declared insurance provider patient related information;

(e) communicating said digital insurance verification request message from the patient health insurance verification computer system to at least one data source located remotely from the patient health insurance verification computer system; and (f) receiving, with the patient health insurance verification computer system from the remotely located data source, a digital insurance verification response message in response to said communicated request message.

2. In a medical facility that utilizes an existing computerized healthcare patient registration computer system to input patient information, the existing computerized healthcare patient registration computer system being used to register patients for healthcare services, the existing computerized healthcare patient registration computer system lacking the capability to reliably verify patient health insurance information in real time, the computerized healthcare patient registration computer system generating digital output signals based at least in part on patient information inputted into the computerized healthcare patient registration computer system, the digital output signals providing patient related information including a declared insurance provider, a method of automatically, without requiring direct human intervention, verifying patient health insurance information using a patient health insurance verification computer system operatively connected to the existing computerized healthcare patient registration computer system, the method comprising the following steps:

(a) operatively connecting a patient health insurance verification computer system to the computerized healthcare patient registration computer system;

(b) capturing at least some patient related information including the declared insurance provider from the digital output signals generated by the computerized healthcare patient registration computer system, (c) generating a digital verification request message based at least in part on said captured patient related information, including the step of formatting the digital verification request message based at least in part on said declared insurance provider;

(d) communicating said digital verification request message to a verification institution;

(e) receiving a digital verification response message in response to said communicated digital verification request message;

(f) providing an indication of at least one aspect of said patient's health insurance to said patient's health care provider in response to said received response message; and (g) discharging said patient from said health care provider some time after said step (f) has been performed.

3. A method as in claim 1 wherein step (c) comprises intercepting a print digital output stream the computerized healthcare patient registration computer sends to a printer attached thereto.

4. A method as in claim 1 wherein step (c) comprises intercepting the digital output stream from a data tap connected between the computerized healthcare patient registration computer and the output device.

5. A method as in claim 1 further including the step of selecting, based on the extracted patient related information, a data source from a set of multiple data sources; and wherein the communicating step (e) comprises:

(e1) establishing a telecommunications connection to the selected data source, and (e2) communicating the digital insurance verification request message to the selected data source over the telecommunications connection established by step (e1).

6. A method as in claim 5 further including the steps of:

maintaining, with the patient health insurance verification computer system, a list of the multiple data sources within the set;

establishing a further telecommunications connection between the patient health insurance verification computer system and a further computer remote thereto; and updating, with the further computer over the established further telecommunications connection, the list of multiple data sources.

7. A method as in claim 1 further including the step of determining an insurance carrier based on the extracted patient related information, and wherein the generating step (d) includes the step of formatting the digital insurance verification message in a predetermined manner associated with the determined insurance carrier.

8. A method as in claim 1 wherein step (e) is performed in real time with performance of step (a).

9. A method as in claim 1 wherein step (c) comprises extracting at least the patient's name and insurance carrier identification from the digital output stream, and generating step (d) comprises selecting a predetermined digital insurance verification request message format based at least in part on the extracted insurance carrier identification.

10. A method as in claim 1 wherein the step (c) comprises extracting at least the patient's name and insurance carrier identification from the digital output stream, and communicating step (e) comprises using a predetermined digital insurance verification request message communications protocol selected based at least in part on the extracted insurance carrier identification.

11. A method as in claim 1 wherein steps (c)–(f) are performed without requiring any human interaction.

12. A method as in claim 1 wherein the method further includes:

(g) maintaining communications information specifying how to communicate with plural data sources, and (h) remotely updating the communications information maintained by step (g); and wherein communicating step (e) includes the step of using at least some of the maintained communications information to communicate the digital insurance verification request message.

13. A method as in claim 1 wherein steps (a)–(d) are repeated for plural different patients to generate plural corresponding different digital insurance verification request messages, and step (e) communicates a batch comprising the plural different digital insurance verification request messages to the data source.

14. A method as in claim 1 wherein step (c) includes the step of extracting at least three of the following data items from the digital output stream:

(1) patient identification;

(2) patient date of birth;

(3) patient sex;

(4) benefit code;

(5) insured identification; and (6) payor identification.

15. A method as in claim 1 wherein step (e) is performed concurrently to communicate multiple digital insurance verification request messages to plural different data sources.

16. A method as in claim 1 further including:

(g) maintaining a log of digital insurance verification request messages generated by step (d); and (h) accessing the log to prevent redundant digital insurance verification request messages from being communicated.

17. A method as in claim 1 wherein step (f) comprises the step of receiving, within the digital insurance verification response message, at least one of:

information concerning particular benefits packages, an indication of whether the health care provider is a member of the patient's managed care group, and copayment arrangements.

18. Apparatus for automatically verifying patient health insurance information in a health care facility having an existing computerized healthcare patient registration computer system including at least one output device connected thereto, the computerized healthcare patient registration computer system being used to register patients for healthcare services by inputting information relating to a patient to be registered with a health care provider, the existing computerized healthcare patient registration computer system lacking the capability to reliably verify patient health insurance coverage information in real time, the computerized healthcare patient registration computer system generating a digital output stream including a declared insurance provider based at least in part on said inputted information, and sending the digital output stream to the output device, the apparatus comprising a patient health insurance verification computer system operatively connected to the existing computerized healthcare patient registration computer system, the patient health insurance verification computer system automatically verifying patient health insurance information without requiring direct human intervention, the patient health insurance verification computer system including:

a capture subsystem that obtains the digital output stream generated by the existing computerized healthcare patient registration computer system and extracts at least some patient related information including the declared insurance provider from said digital output stream, a communications subsystem that generates a digital insurance verification request message formatted based at least in part on said extracted declared insurance provider patient related information, communicates said digital insurance verification request message from the patient health insurance verification computer system to at least one data source located remotely from the patient health insurance verification computer system, and receives, from the remotely located data source, a digital insurance verification response message in response to said communicated request message, and an indicating subsystem that provides a humanly readable indication of the received digital insurance verification response message.

* * * * *